United States Patent
Tripp et al.

(10) Patent No.: US 6,569,676 B1
(45) Date of Patent: May 27, 2003

(54) STORAGE AND SHIPPING APPARATUS FOR CULTURES AND SPECIMENS

(75) Inventors: Patricia D. Tripp, Bluefield, VA (US); Kathleen M. Belcher, Mount Juliet, TN (US)

(73) Assignee: Innovative Genetic Technology, L.L.C., Mt. Juliet, TN (US)

( * ) Notice: Subject to any disclaimer, the term of this patent is extended or adjusted under 35 U.S.C. 154(b) by 0 days.

(21) Appl. No.: 09/629,268

(22) Filed: Jul. 31, 2000

(51) Int. Cl.[7] ................................................ C12M 1/00
(52) U.S. Cl. ................ 435/307.1; 422/102; 435/304.1; 435/307.1; 206/438; 206/459.5; 206/569; 206/572; 229/120.02
(58) Field of Search ................................ 436/807–810; 422/102; 435/288.1, 304.1, 307.1; 206/569, 571, 572, 204, 438, 459.5; 229/141, 147, 120.37, 120.02

(56) References Cited

U.S. PATENT DOCUMENTS

| | | | |
|---|---|---|---|
| 3,759,375 A | 9/1973 | Nappi | 206/63.2 R |
| 3,915,806 A | 10/1975 | Horlach | 195/139 |
| 4,175,008 A | 11/1979 | White | 435/295 |
| 4,195,059 A * | 3/1980 | Whitcher et al. | 422/61 |
| 4,586,604 A | 5/1986 | Alter | 206/210 |
| 4,689,099 A | 8/1987 | Ito et al. | 156/69 |
| 4,877,036 A | 10/1989 | Saint-Amand | 128/749 |
| 4,898,278 A * | 2/1990 | Leoncavallo et al. | 206/443 |
| 4,903,708 A | 2/1990 | Saint-Amand | 128/749 |
| 5,101,970 A | 4/1992 | Turner | 206/223 |
| 5,211,286 A | 5/1993 | Turner | 206/223 |
| 5,330,056 A | 7/1994 | de la Rocha | 206/581 |
| 5,586,653 A | 12/1996 | Taveroff | 206/362 |
| 5,645,990 A | 7/1997 | Love | 435/6 |
| 5,695,930 A | 12/1997 | Weinstein et al. | 435/5 |
| 5,787,891 A | 8/1998 | Sak | 128/756 |
| 5,824,471 A | 10/1998 | Mashal et al. | 435/6 |
| 5,833,057 A * | 11/1998 | Char et al. | 206/204 |

* cited by examiner

Primary Examiner—David A. Redding
(74) Attorney, Agent, or Firm—Womble Carlyle Sandridge & Rice, PLLC

(57) ABSTRACT

An apparatus for storing and shipping a coded set of related culture specimens without risk of contamination or contact between individually coded specimens, comprising a closeable case having multiple individual storage cells and a coding scheme applied to the surfaces of the case. The coding scheme identifies and matches individually coded specimens with their respective storage cells.

1 Claim, 5 Drawing Sheets

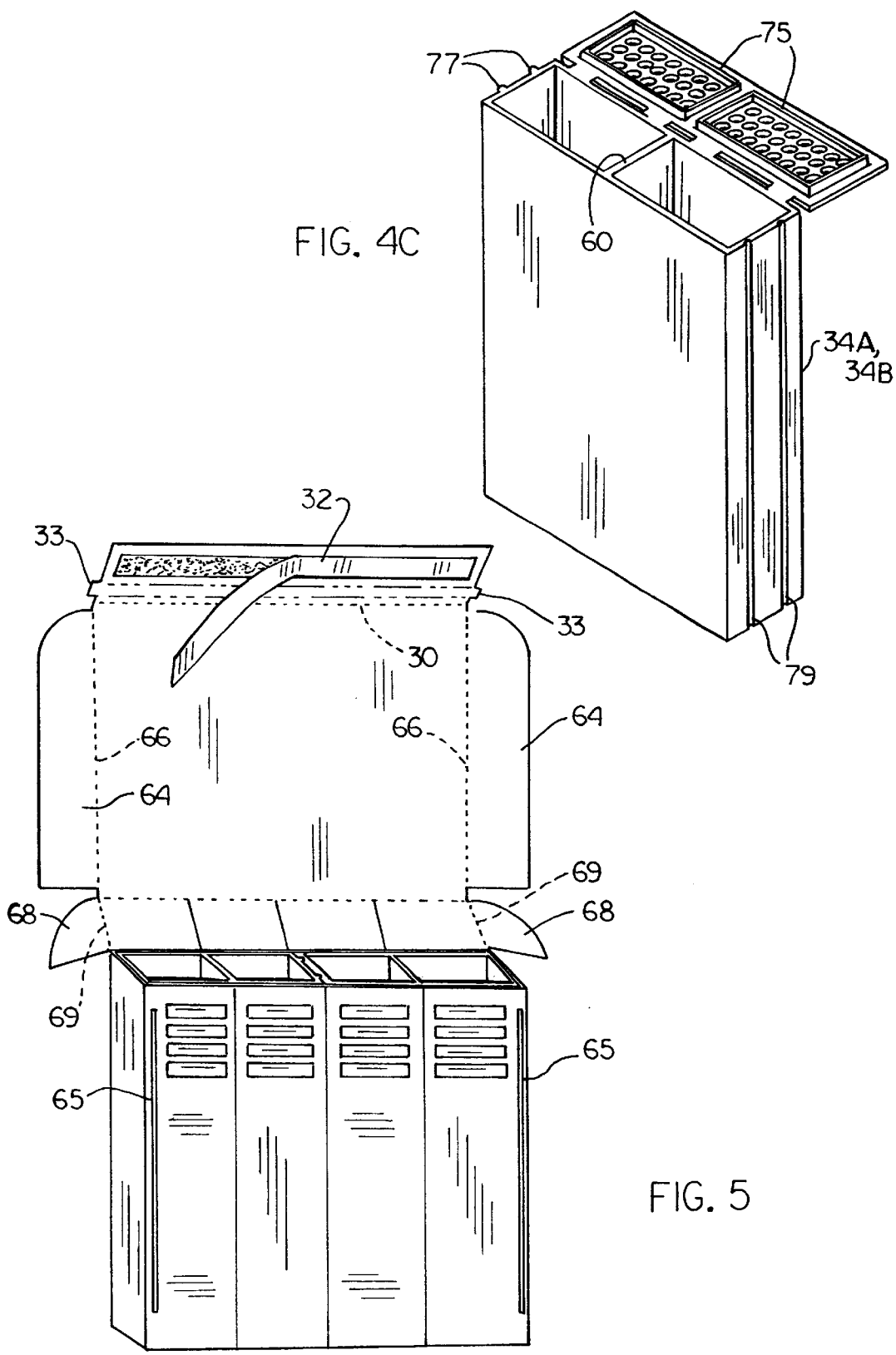

STORAGE AND SHIPPING APPARATUS FOR CULTURES AND SPECIMENS

BACKGROUND OF THE INVENTION

The present invention relates generally to the storage and shipment of a related set of cell cultures or specimens and, more particularly, to a storage and shipping container for specimen swabs that minimizes the possibility of mislabeling or intermingling the swabs comprising the set, while eliminating bacterial or fungal growth through proper drying.

For a variety of reasons, cell cultures or specimens are taken from a person and shipped to a laboratory facility where identification and testing of the cultures or specimens is undertaken. This testing may relate to the diagnosis and treatment of illnesses, or may be done for DNA research for, among other things, paternity testing or transplant matching. Commonly, prepackaged sterilized swabs are used in the collection of specimens. Upon taking the specimens, they are typically returned to individual storage envelopes or other packaging and transported individually to the laboratory facility.

While individually packaging and shipping specimens is desirable in some applications, the specimens taken from several different samples or individuals may actually comprise a set for identification and testing purposes. Such is the case, for example, in paternity testing where specimens from the mother, child, and one or more imputed fathers may comprise the set of interest.

The prior art discloses a specimen holding kit for transporting a single cell specimen in a saturated medium. There is also known a method and apparatus for sampling cervical tissue wherein a swab is sold as part of a test kit. Once a sample is taken, the swab is stored in an airtight plastic container for shipment to a laboratory. While kits for a variety of tests, including paternity, are known, none teach the use of a specialized case for holding samples from a related set of individuals separate from each other, but within the same container.

SUMMARY OF THE INVENTION

The present invention is directed to a specimen storage and shipping apparatus wherein a set of related specimens, such as buccal swabs, can be placed in individual cells without risk of contact or contamination, yet be stored and/or shipped as a set to a laboratory facility. Also, there may be provided a simplified coding scheme for identifying and matching individual specimens with their respective storage cells. The risks of losing an individual specimen or compromising the integrity of the specimen set is thus minimized.

Accordingly, one embodiment of the present invention is a storage and shipping case for receiving a separately formed cartridge having a plurality of storage cells. The storage and shipping case is comprised of a paperboard or fiberboard container having a bottom, an open top, a front wall, a rear wall, and sidewalls. Each of the outer wall surfaces is suitable for printing or other indicia. The outer surface areas of the case adjacent each cartridge storage cell are appropriately coded. One form of coding is color; however, other codes, such as numbers, may be used. A closure panel is connected to the top edge of either the rear or front wall of the storage and shipping case and is formed such that, when the closure panel is folded along fold lines in the panel, the panel closes the open top of the container. Desirably also, a portion of the closure panel inner surface area adjacent each cartridge storage cell is colored to correspond to the color on the outer surface of the shipping and storage case.

The cartridge is contained within the storage and shipping case. The cartridge may be integrally formed, having a bottom, an open top, a front wall, a rear wall, sidewalls, and multiple integrally formed dividers separating the cartridge into individual storage cells. Each storage cell is dimensioned to hold at least two swabs/specimens taken from the same person. Alternatively, the cartridge may be comprised of multiple integrally formed containers arranged adjacently together, where each container has one or more individual storage cells. Desirably, the cartridge is formed of a semi-rigid, leak-resistant material such as polypropylene. However, other suitable materials having these characteristics may be used. The cartridge, or integrally formed containers, may have vented closures for the cartridge or container as a whole or for the individual storage cells. These ventilated closures provide an additional measure of closure for the storage and shipping container and allow for ventilation and drying of the swabs contained within each storage cell. Further, once the specimens are collected from an individual and placed in the appropriate storage cell, the vented closure may be closed to prevent the specimens from another individual being inadvertently placed in the same cell. The integrally formed or composite cartridge is substantially the same shape as the storage and shipping case, but is preferably slightly smaller in overall dimensions such that documentation pertaining to the enclosed specimens can be placed between the front or rear wall of the storage and shipping case and the adjacent cartridge front or rear wall.

In the second embodiment, the storage and shipping case includes integrally formed dividers that are appropriately provided with a protective coating so that the need for the separate cartridge is obviated. The case then includes built-in storage cells.

Another aspect of the present invention is to provide a method for storing and preparing specimens for shipment as a set. Using coded swabs, a set of specimens is obtained from individuals comprising the test set, where each coded swab is unique to the individual. Desirably, the swabs would be color-coded; e.g., pink for the mother, yellow for the child, blue for the imputed father, and green for an additional child or imputed father, etc. The specimen swabs are placed in their individual storage cells by matching the code on the swabs with the code formed on the surface of the storage and shipping case adjacent each of the storage cells. Any necessary documentation concerning the specimens could be inserted in the storage and shipping case in a space between the cartridge and the storage and shipping case inner wall. Alternatively, where the storage and shipping case includes integrally formed dividers, documentation could be placed in one or more of the storage cells. With all specimens and documentation secured, a closure panel attached to the rear or front wall of the storage and shipping case is folded along fold lines formed in the panel to close the open top of the storage and shipping case.

These and other aspects of the present invention will become apparent to those skilled in the art after a reading of the following description of the preferred embodiment when considered with the drawings.

BRIEF DESCRIPTION OF THE DRAWINGS

FIG. 4C is a front perspective view of an individual case used to form the cartridge of FIG. 4A;

FIG. 5 is a front perspective view of the specimen storage and shipping apparatus of FIG. 1 with closure flaps and a tear strip.

DESCRIPTION OF THE PREFERRED EMBODIMENTS

Figure 1:
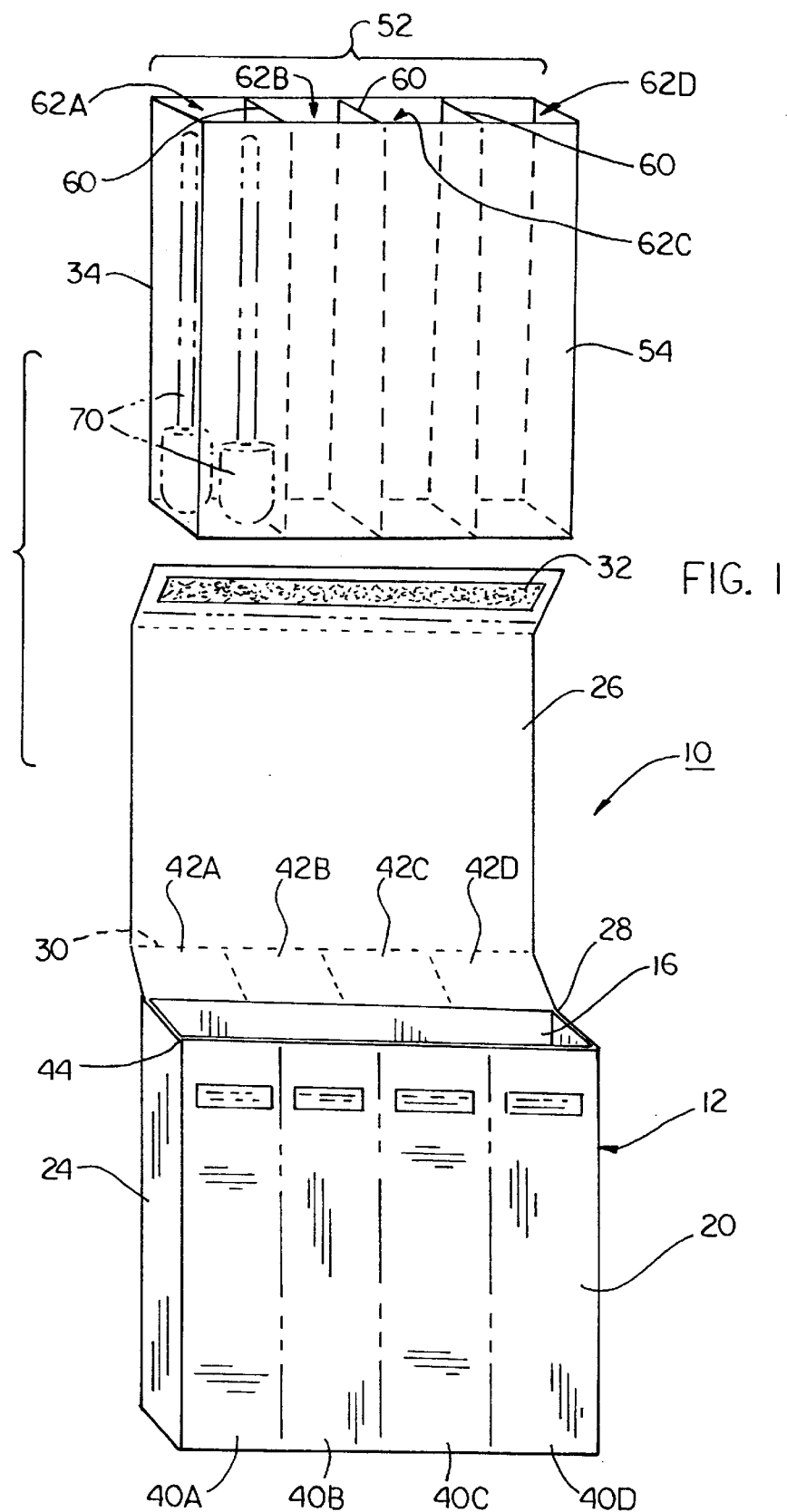
FIG. 1 is a front perspective exploded view of one aspect of the specimen storage and shipping apparatus according to the present invention.
Figure 2:
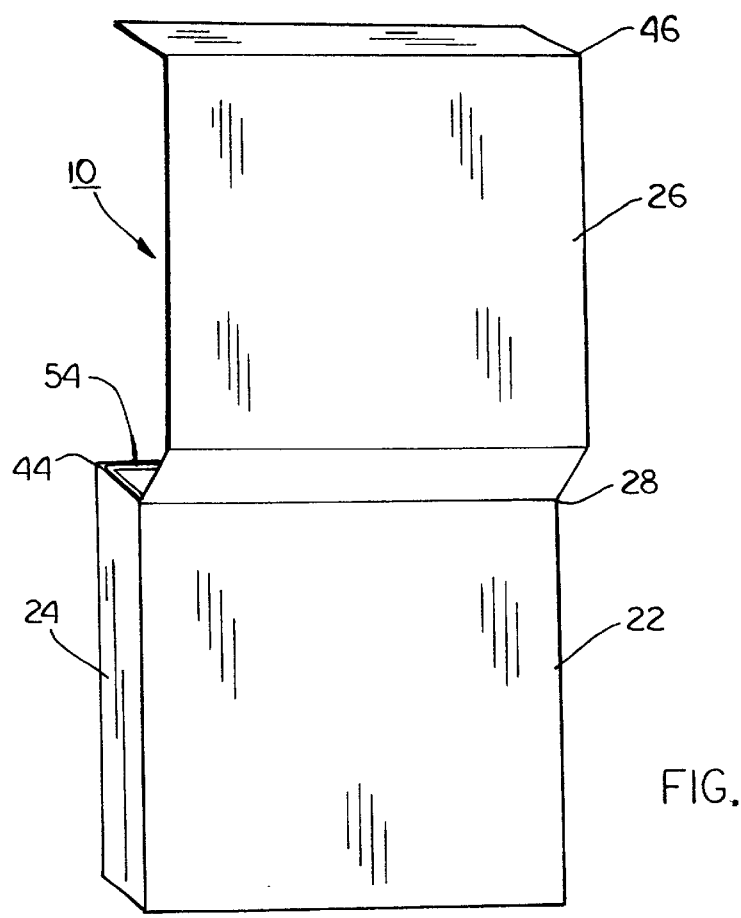
FIG. 2 is a rear perspective view of the specimen storage and shipping apparatus of FIG. 1.
Figure 3:
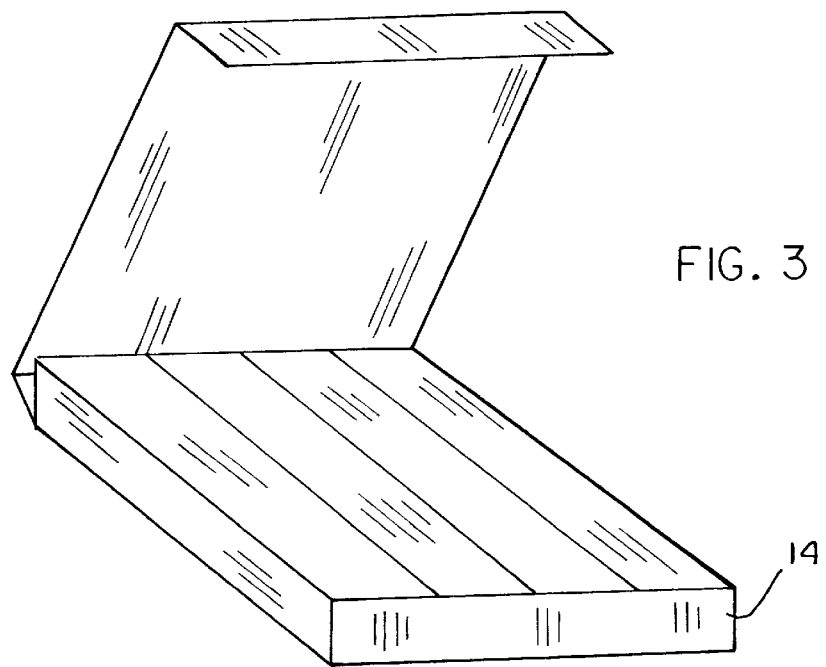
FIG. 3 is a bottom front perspective view of the specimen storage and shipping apparatus of FIG. 1.

Referring now to the drawings in general and FIG. 1 in particular, it will be understood that the illustrations are for the purpose of describing a preferred embodiment of the invention and are not intended to limit the invention thereto. As best seen in FIGS. 1 through 3, a culture specimen storage and shipping apparatus constructed according to one aspect of one embodiment of the present invention, generally designated 10, includes a storage and shipping case 12 and an integrally formed cartridge 34. The storage and shipping case 12 is formed of a paperboard or fiberboard material such that printing or other indicia may be formed on the outer surfaces, but other suitable materials may be used. Storage and shipping case 12 has a bottom 14, open top 16, front wall 20, rear wall 22, and sidewalls 24 A closure panel 26 is hingedly connected to a top edge 28 of front wall 20, or rear wall 22. Closure panel 26 includes fold lines 30 spaced apart such that when closure panel 26 is folded along fold lines 30, closure panel 26 overlies open top 16. Alternatively, closure panel 26 could be formed to overlie front wall 20, or rear wall 22 or could simply include a tuck flap or other suitable closing member to close open top 16. As best seen in FIG. 1, closure panel 26 is connected to the top edge 28 of rear panel 22. Closure panel 26 could be attached to top edge 44 of front wall 20 and folded to overlie open top 16, and if desired, rear wall 22. A seal tab 32 is hingedly attached to the top edge 46 of closure panel 26 along a fold line 30 such thatseal tab 32 may be adhered to the bottom 14 of shipping and storage case 12. Alternatively, closure panel 26 may be constructed such that seal tab 32 is adhered to front wall 20 or rear wall 22. Any suitable adhesive, such as a tape seal, may be used to adhere the seal tab 32 such that the storage and shipping apparatus 10 will remain intact during shipment.

Turning now to FIG. 5, alternatively, storage and shipping case 12 may have closure flaps 64 hingedly attached to edges 66 of closure panel 26. Upon closure of panel 26, closure flaps 64 would be tucked into slits 65 formed through either side of front wall 20 so that flaps 64 would be between front wall 20 and cartridge 34. In addition to, or in lieu of flaps 64, flaps 68 may hingedly attached to edges 69 of closure panel 26. Flaps 68 would be tucked in between side walls 24 and cartridge 34 upon closure of panel 26. Further, for ease in opening a sealed storage and shipping container 10 and removing swabs 70, a tear strip 33 may be formed in dosure panel 26 between fold line 30 and seal tab 32.

Figure 4A:
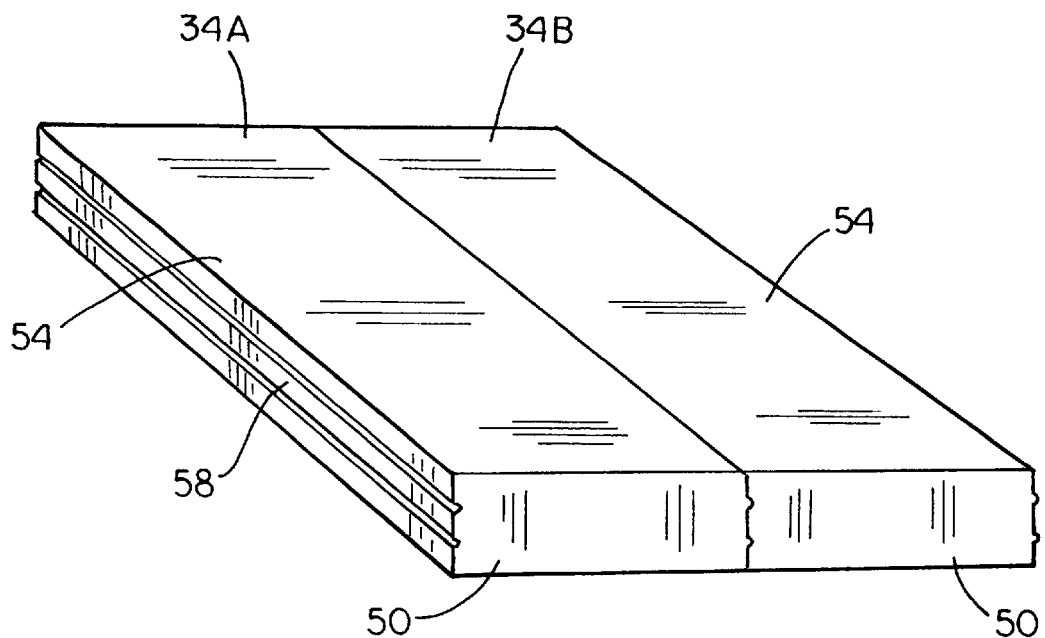
FIG. 4A is a bottom front perspective view of the cartridge according to the present invention.
Figure 4B:
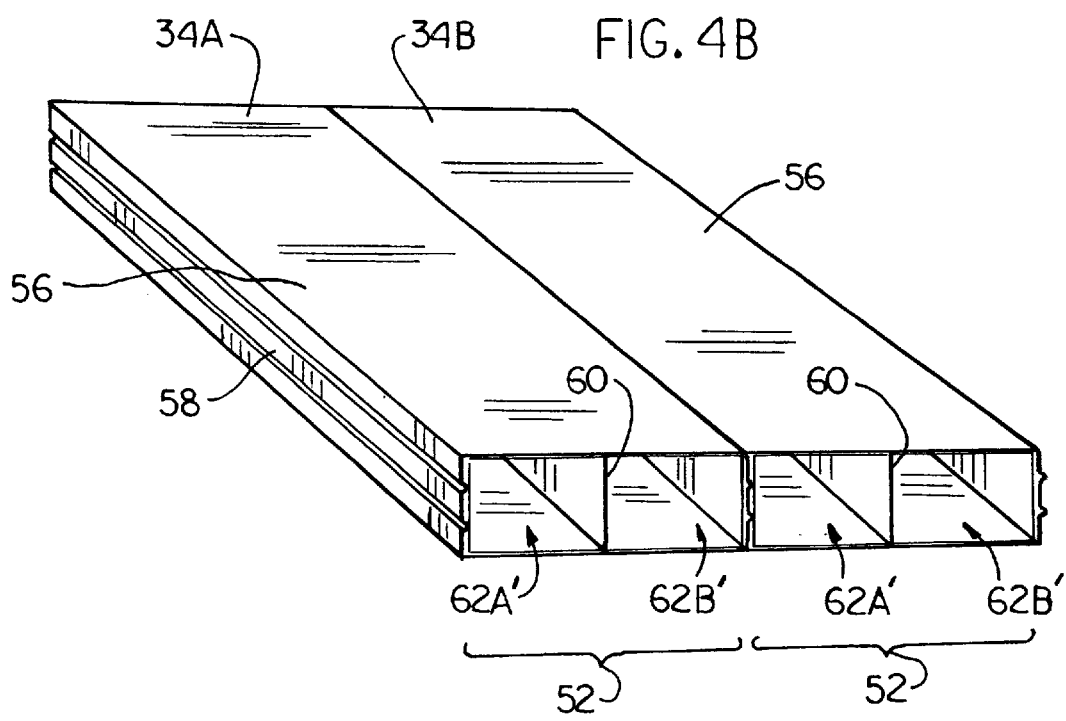
FIG. 4B is a top rear perspective view of the cartridge of FIG. 4A.

In the preferred embodiment, culture specimen storage and shipping apparatus 10 comprises a storage and shipping case 12 for receiving a cartridge 34. Cartridge 34 may be integrally formed as a single unit, or as seen in FIGS. 4A through 4C, may comprise two or more integrally formed containers, shown in the figures as 34A and 34B. Although not necessary to the function or construction of storage and shipping apparatus 10, containers 34A and 34B may be fastened together by interlocking ribs 77 on one case with channels 79 on the adjacent case. Ribs 77 and channels 79 may be formed in a variety of ways known in the art for interlocking or snapping like units together. Each container 34A, 34B has a bottom 50, an open top 52, front wall 54, rear wall 56, sidewalls 58, and may have integrally formed dividers 60, separating each container 34A, 34B into a plurality of individual storage cells 62A', 62B'. Each cell 62A', 62B' is dimensioned to hold at least two specimens, or swabs, obtained from the same person. As best seen in FIG. 4C, cartridge 34, or alternatively, adjacent containers 34A, 34B may have vented closures 75 integrally formed with and hingedly attached to open ends 52. Vented closures 75 may be formed to cover the entire open end 52 or, alternatively, formed to cover individual cell 62A', 62B'. Vented closures 75 are formed to interlock or otherwise snap into place over the open ends of cells 62A', 62B'. The vented closures 75 provide an additional measure of closure for the storage and shipping apparatus 10 and permit adequate ventilation and drying of swabs 70 stored within cells 62A' and 62B'. To achieve adequate ventilation, each vent closure 75 comprises at least 50 percent perforated area. However, desirably, perforations in vented closures 75 are dimensioned small enough to prevent the stem of a swab 70 in a cell 62A', 62B' from sticking therethrough.

As best seen in FIG. 1, in the preferred embodiment, front wall 20 is coded such that areas 40A, 40B, 40C, and 40D are each coded differently; e.g., a different color, to correspond to individual storage cells 62A, 62B, 62C, and 62D. Similarly, areas 42A, 42B, 42C, and 42D are coded to correspond to the same coding scheme as 40A, 40B, 40C, and 40D. Accordingly, coded specimen swabs 70, such as that illustrated in FIG. 1, can be matched to their respective coded storage cells.

The dimensions of the composite cartridge 34 are desirably slightly smaller than the overall dimensions of storage and shipping case 12 such that documentation relating to the specimens may be inserted between cartridge 34 and the inner surface of either front wall 20 or rear wall 22 of storage and shipping case 12.

Figure 6:
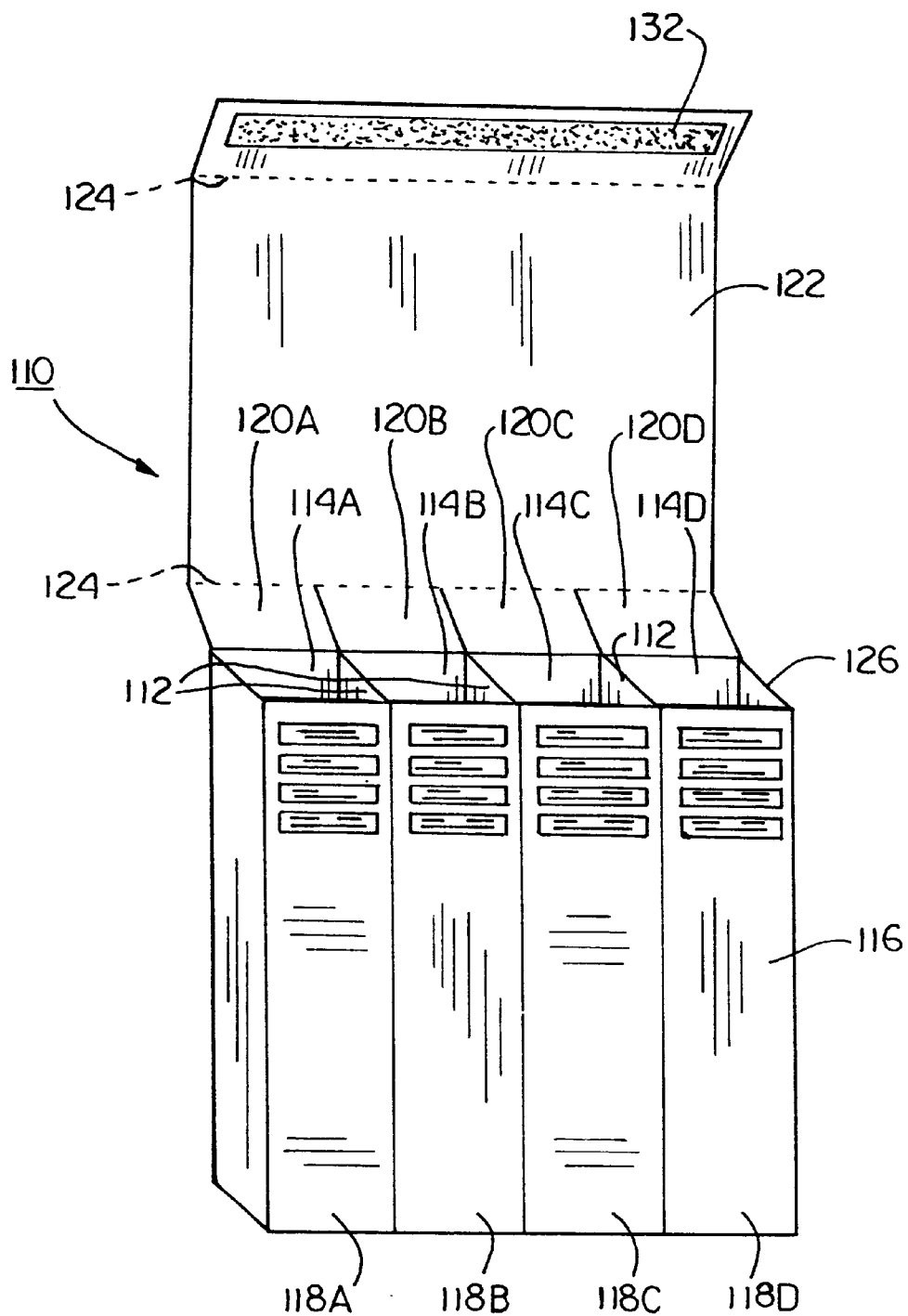
FIG. 6 is a front perspective view of the specimen storage and shipping apparatus with integrally formed dividers.

Referring to FIG. 6, as an alternative to the separate case 12 and cartridge 34, storage and shipping apparatus 110 may be formed such that dividers 112 are an integrally formed part of the storage and shipping apparatus 110. In this embodiment, storage and shipping apparatus 110 is formed of a paperboard or fiberboard material and dividers 112 are provided with a protective coating to prevent communication between individual storage cells 114A, 114B, 114C, and 114D. In this embodiment, front wall 116 is coded such that areas 118A, 118B, 118C, and 118D are each coded; e.g., a different color, to correspond to individual storage cells 114A, 114B, 114C, and 114D. Similarly, areas 120A, 120B, 120C, and 120D are coded to correspond to the same codes as 118A, 118B, 118C, and 118D. A closure panel 122 includes fold lines 124 spaced apart such that when closure panel 122 is folded along fold lines 124, closure panel 122 will overlie front wall 116.

In storing and preparing a set of culture specimens for shipment, a user would first obtain individual specimens using suitable coded specimen swabs. The swabs would be placed individually in storage cells 62 or 114. If desired, documentation pertaining to the specimens could be inserted in storage and shipping case 12 between cartridge 34 and front wall 20, or rear wall 22. Alternatively, where storage and shipping apparatus 110 has integrally formed dividers 112, documentation may be placed in the individual storage cells 114. The shipping and storage apparatus 10, 110 would then be closed by folding closure panel 26, 122 along fold lines 30, 124 whereupon closure panel 26, 122 would cover open top 16, 126, of storage and shipping apparatus 10, 110. Storage and shipping apparatus 10, 110 is then ready to be transported to a laboratory facility.

Certain modifications and improvements will occur to those skilled in the art upon a reading of the foregoing description. It should be understood that all such modifications and improvements have been deleted herein for the sake of conciseness and readability but are properly within the scope of the following claims.

We claim:
1. An apparatus for storing and shipping a coded set of related culture specimens without risk of contamination or contact between individually coded specimens, comprising:
    (a) a closeable case for receiving a cartridge, said case having surfaces for applying a coding scheme thereon;
    (b) a coding scheme applied to said surfaces of said case;
    (c) a cartridge formed of polypropylene and comprised of a plurality of integrally formed containers placed in said case in adjacent arrangement, said integrally formed containers each having one or more individual storage cells; and
    (d) wherein when said cartridge is received in said case, said coding scheme identifies and matches individually coded specimens with their respective storage cells.

* * * * *